United States Patent [19]

Wittwer et al.

[11] Patent Number: 4,539,060
[45] Date of Patent: Sep. 3, 1985

[54] APPARATUS AND METHOD OF SEALING CAPSULES

[75] Inventors: Fritz Wittwer, Lupsingen; Ivan Tomka, Bourguillon, both of Switzerland

[73] Assignee: Warner-Lambert Company, Morris Plains, N.J.

[21] Appl. No.: 468,022

[22] Filed: Feb. 18, 1983

[51] Int. Cl.³ .............................................. C09J 27/02
[52] U.S. Cl. .................... 156/275.1; 156/69; 156/305; 156/381; 156/578; 206/530; 427/3; 427/45.1
[58] Field of Search ................. 53/485; 156/69, 272.2, 156/272.8, 275.1, 305, 381, 578; 206/528, 530; 427/256, 430.1, 3, 45.1

[56] References Cited

U.S. PATENT DOCUMENTS

| | | | |
|---|---|---|---|
| 3,071,513 | 1/1963 | DeBoer et al. | 53/485 X |
| 3,164,508 | 1/1965 | Marcer | 156/274.8 |
| 3,769,117 | 10/1973 | Bowen et al. | 219/121 LD X |
| 4,281,763 | 8/1981 | Pace | 206/530 |

Primary Examiner—Robert A. Dawson
Attorney, Agent, or Firm—Alan H. Spencer; Stephen Raines

[57] ABSTRACT

Methods are disclosed for the sealing of gelatin capsules having hard shell coaxial cap and body parts which overlap when telescopically joined. Also described are apparatus and sealing fluids to seal the capsules.

15 Claims, 5 Drawing Figures

APPARATUS AND METHOD OF SEALING CAPSULES

BACKGROUND OF THE INVENTION

1. FIELD OF THE INVENTION

This invention relates to methods for sealing capsules, using sealing fluids, and/or thermal energy; and apparatus for sealing such capsules.

The capsules sealed by utilizing the present invention are hard shell, telescopically joined capsules, having coaxial cap and body parts. The capsules are made of gelatin or other materials whose properties are pharmaceutically acceptable.

In this application, when the term "gelatin" is used it is also understood to include gelatin combined with other hydrophilic polymers.

Capsules were sealed having a cap and/or body part made from a gelatin foam as disclosed in applicant's copending application U.S. Ser. No. 438,147 filed Oct. 29, 1982, now abandoned, the disclosure of which is incorporated herein by reference.

In addition, capsules were sealed by sealing fluids as disclosed in applicant's copending application U.S. Ser. No. 451,580, filed Dec. 20, 1982, now abandoned, the disclosure of which is incorporated herein by reference.

Hard shell gelatin capsules have a disadvantage when compared with other dosage forms, in that the cap and the body parts can be opened and rejoined without the disruption becoming externally visible or tamper-evident. Therefore, the consumer has no real guarantee that the contents of a capsule have not been tampered with.

Telescopically joined, hard shell gelatin capsules have an overlap of the cap side wall over the body side wall which impedes gripping and withdrawal of the body, thereby making separation difficult. The present invention uses sealing fluid and/or thermal energy applied to the overlap of the cap side wall over the body side wall to secure tamper-proofing by spot or complete sealing of the overlap of the capsule parts. With the use of a complete sealing, the capsules are also tight against leakage of liquid contents.

2. DESCRIPTION OF THE PRIOR ART

Prior art for capsule sealing is contained in the following United States patents:

1. U.S. Pat. No. 3,071,513 issued Jan. 1, 1963 to H. R. De Boer, et al. which discloses a sealing fluid comprising a dispersion of an air-drying hydrophilic, film-forming polymer in an organic solvent. The application of the sealing fluid was by dipping the capsules:

2. U.S. Pat. No. 3,159,546 issued Dec. 1, 1974 to J. R. Kane discloses a liquid sealant consisting of three components containing by weight from about 1 to 4½ parts, preferably 3 to 4½ parts, of acetone; from about 1½ to 2 parts, and preferably 1¼ to 2 parts, of water; and from about ¾ to 2¼ parts, and preferably about ¾ of a part, of ethyl acetate. The application of the liquid solvent was by drop application.

BRIEF DESCRIPTION OF THE DRAWINGS

The apparatus and methods of the present invention are described in the following drawings.

OPERATION OF THE APPARATUS FOR SEALING CAPSULES

Figure 1:
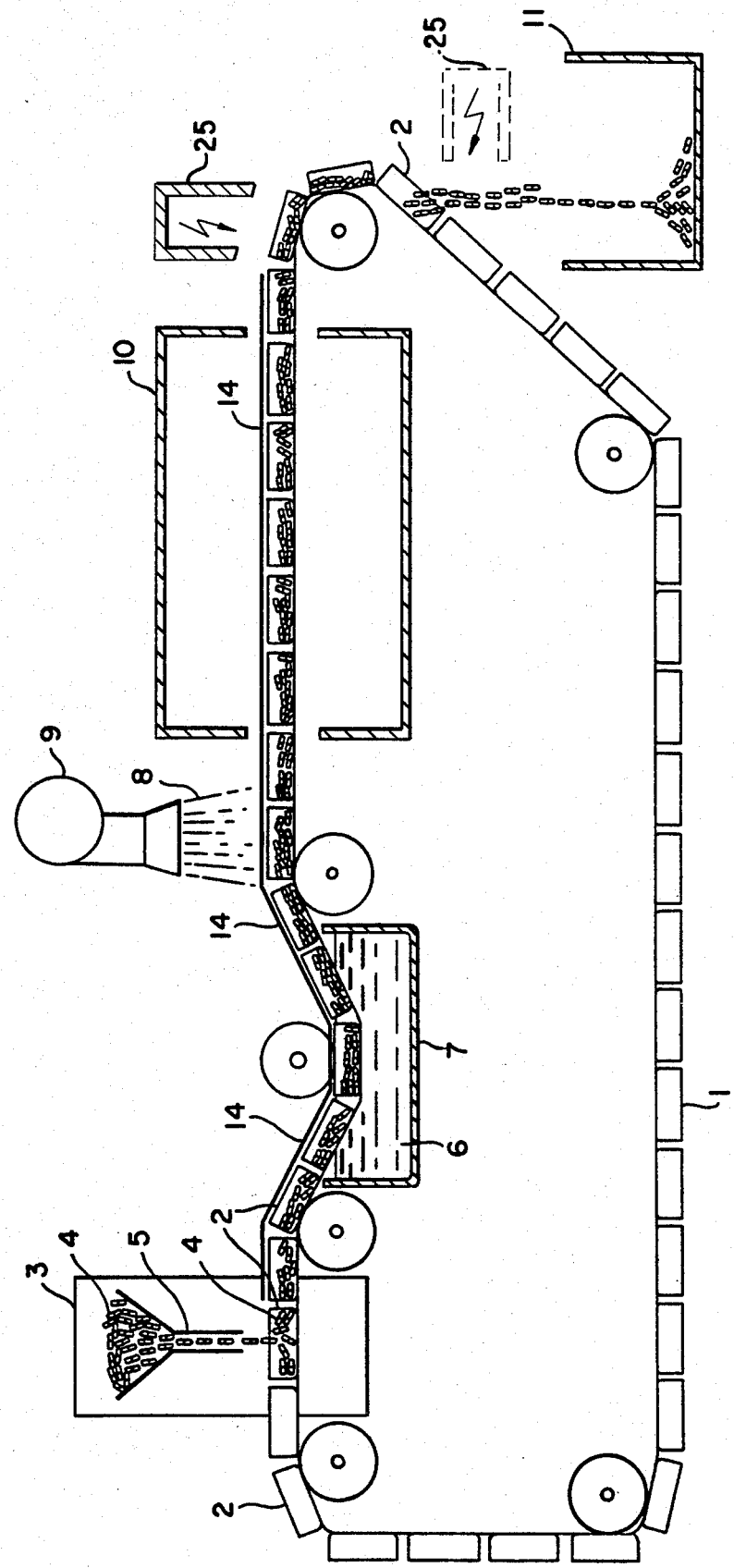
FIG. 1 shows a schematic of a continuous conveyor 1 having net or wire mesh baskets 2. A capsule filling machine 3 ejects filled and telescopically joined hard shell gelatin capsules 4 through a funnel 5 into the mesh baskets 2 which pass beneath the funnel 5. The capsules 4 are randomly oriented in the mesh baskets 2, which capsules 4 are then dipped into a sealing fluid 6 contained in a dipping tank 7. It is essential that the overlap of the cap and body side walls of each capsule 4 come into contact with the sealing fluid 6. Thereafter, the capsules 4 are conveyed through a drying stream of conditioned air 8 from a blower 9 located above or below the capsules 4 in order to remove excess sealing fluid 6 from the surface of the capsules 4 so as to avoid deformation and sticking together of the capsules 4. However, the sealing fluid is removed only from the surface, and not from within the overlapping seal of each capsule. The surface dried capsules 4 are then heated by a specific energy source applying a defined quantity of thermal energy, located after the dryer 10 or at the ejection of capsules 4 from the conveyor 1. The dryer 10 may be a kiln; an oven; a tumbler dryer; etc. Thereafter, the capsules 4 are conveyed to and ejected into a capsule container 11 for further processing and shipment. A cover 14 is provided over the mesh baskets 2 to prevent floating-away or blowing-away of the capsules 4 during processing between the funnel 5 and the dryer 10.

The sealing of capsules in the present invention is accomplished as follows:

The sealing fluid is evenly distributed between the overlap of the cap and body side walls of the gelatin capsule by capillary effect. This effect is achieved when the contact angle between a drop of the sealing fluid and the gelatin film is small, e.g. if the wettability of the gelatin film is high, the contact angle can be reduced by the addition of surfactants.

The mechanism of the capillary effect is described by Walter J. Moore in Physical Chemistry, 4th Edition, pages 479-481, Longman Edition, London, England, (1978) as follows: "Whether a liquid rises in a glass capillary depends on the relative magnitude of the forces of adhesion between the liquid molecules themselves, and the forces of adhesion between the liquid and the walls of the tube. These forces determine the contact angle, which the liquid makes with the tube walls. If this angle is less than 90 degree, the liquid is said to wet the surface and a concave meniscus if formed."

The wettability of gelatin films is measured as "adhesional wetting" where a liquid not originally in contact with a substrate makes contact with that substrate and adheres to it.

The contact angles between gelatin films and solvents were measured for a number of sealing fluids of the present invention by use of a microscope fitted with a goniometer eyepiece.

The tests were performed on a gelatin film whereby the contact angle was measured 20 seconds after depositing a drop of sealing fluid on the gelatine film. The following Table I shows contact angles of sealing fluids of the present invention:

TABLE I

| Sealing Fluids | Mean Contact Angles |
| --- | --- |
| Water | 83° ± 6° |
| 75% aqueous ethyl alcohol solution | 3.5° ± 1° |
| 75% ethyl alcohol solution mixed with an aqueous solution of 0.5 M $CaCl_2$ and $^1$M KI | near to 0° (not detectable) |
| 90% aqueous methanol solution | near to 0° (not detectable) |
| Water containing 0.1% sodium lauryl sulfate | 51° |
| Water containing 0.5% of a hydrolyzed gelatin and 0.1% of sodium lauryl sulfate | 66° |
| Water containing 0.2 M $Na_2SO_4$ and 0.1% sodium lauryl sulfate | 43° |
| Water containing 1% polyvinylpyrrolidone and 0.1% of sodium lauryl sulfate | 64° |

The sealing fluid dissolves the amorphous part of the gelatine between the overlap of the cap side walls over the body side walls of the capsules by lowering the glass transition temperature of the gelatin. Furthermore, the sealing fluid may partially depress the melting point of the crystalline part of the gelatin. The melting point of the crystalline part of the gelatin may, however, mainly be depressed below room temperature by solvents, which are known as hydrogen bond breakers. These solvents are, however, not edible (urea, formamide, N-methylformamide, dimethylformamide). In order to achieve better sealing the melting of the crystalline part of the gelatin may be affected by raising the temperature of the gelatin above its melting point. This may be achieved by the input of thermal energy. Another important effect, due to the application of thermal energy, preferably with convection heat, is the shrinkage of the overlap of the cap with the body of the capsule, resulting in a complete contact of the peptized wall surface of the overlap, thus achieving a better seam. The reason for this is that the gelatin changes its specific volume during the abovementioned process. The input of thermal energy can be accomplished by conduction due to contacting the overlapping seam with the warm surface of a solid, i.e. by metal coated with Teflon ®, heated to 120° to 180° C.; or circulating a warm gas at a temperature of about 70° to 140° c., around the capsule; or by putting the capsules in the field of electromagnetic irradiation preferentially in the infrared or microwave range of the frequency spectrum. The input of energy may be localized to the part of the capsule i.e. the overlapping seam, where the sealing is taking place. This can be achieved by irradiating electromagnetic energy at a frequency range whereby the sealing fluid preferentially absorbs this energy in the form of heat. One embodiment to realize this is to irradiate electromagnetic energy at 2.4 GHz in the presence of water as a sealing fluid. However, the dry gelatin swells in the presence of water in much too short a time to be applicable otherwise than locally at the overlap of cap and body parts of the capsule. To circumvent this, one dips the capsules in various aqueous and/or organic sealing fluids and blows off the excess sealing fluid from the surface of the capsules; leaving the fluid only between the overlap of the body and the cap parts of the capsule. Another embodiment to localize the thermal energy at the overlapping seam can be achieved by the application of energy through a slit of an insulating plate under which the capsule is positioned and axially rotated in a way that only the overlapping seam part is exposed to the thermal energy. Sources of energy can be radiation (microwaves or infrared) or convection heating. Organic solvents, which are sufficiently miscible with water but reduce the swelling ability of water to a proper degree are given in the following groups of sealing fluids:

In general, the sealing fluids used in the present invention contain a considerable amount of water. A denaturation and peptization of the gelatin is a necessary effect for the present invention. This effect can be achieved by the application of a localized thermal energy source to following 4 Groups of sealing fluids to the capsule seam:

1. Organic Solvents

Sealing fluids of organic solvents having a solubility parameter between about 10 to about 23.4; and being sufficiently miscible with water at a pH range between 1 to 13 are given in TABLE 2 below, based on the following References:

J. Brandrupp and E. H. Immergut, Polymer Handbook, 1st Edition, pages IV 356-358, John Wiley N.Y. (1966)

J. Bello et al, J. Phys. Chem 60, page 1299, (1956)

TABLE 2

| $\Delta(cal/cc)^{\frac{1}{2}}$ | Organic Solvent |
| --- | --- |
| 10.0 | amyl alcohol (iso) |
| 10.0 | carbon disulfide |
| 10.0 | dichlorobenzene (ortho) |
| 10.0 | diethyl phthalate |
| 10.0 | dimethyl 1-2,2-butanediol-1.3 |
| 10.0 | dioxane-1,4 |
| 10.0 | dipropylene glycol |
| 10.0 | ethylamine |
| 10.0 | ethylene glycol diacetate |
| 10.0 | ethyl lactate |
| 10.0 | methyl isobutyl carbinol |
| 10.0 | nitrobenzene |
| 10.0 | propionic anhydride |
| 10.1 | acetic acid |
| 10.1 | caprolactone |
| 10.1 | dibromoethylene-1,2 |
| 10.1 | propylene glycol methyl ether |

TABLE 2-continued

| Δ(cal/cc)^½ | Organic Solvent |
|---|---|
| 10.2 | cresol (meta) |
| 10.2 | diethylene glycol monoethyl ether |
| 10.2 | dioxolane-1,3 |
| 10.2 | methyl formate |
| 10.2 | methyl iodine |
| 10.3 | acetaldehyde |
| 10.3 | acetic anhydride |
| 10.3 | aniline |
| 10.3 | butyric acid (iso) |
| 10.3 | hexanediol-2,5 |
| 10.3 | methyl-2-pentanediol-1,3 |
| 10.3 | nitro-1-propane |
| 10.3 | octyl alcohol (normal) |
| 10.4 | cyclopentanone |
| 10.4 | dibromoethane-1,2 |
| 10.5 | acrylonitrile |
| 10.5 | butyl alcohol (iso) |
| 10.5 | butyric acid (normal) |
| 10.5 | butyronitrile |
| 10.5 | ethyl-2-butanol-1 |
| 10.5 | ethylene glycol monoethyl ether |
| 10.5 | hexamethylphosphoramide |
| 10.5 | methyl benzoate |
| 10.6 | bromonapthalene |
| 10.6 | butyl alcohol (tert.) |
| 10.6 | diethylformamide (N,N) |
| 10.6 | heptyl alcohol (normal) |
| 10.6 | methyl salicylate |
| 10.7 | dimethyl phthalate |
| 10.7 | hexyl alcohol (normal) |
| 10.7 | pyridine |
| 10.7 | triethylene glycol |
| 10.8 | butyl alcohol (secondary) |
| 10.8 | dimethylacetamide (N,N) |
| 10.8 | pentanediol-2,4 |
| 10.8 | propionitrile |
| 10.8 | quinoline |
| 10.9 | amyl alcohol (normal) |
| 11.0 | cyclobutanedione |
| 11.0 | dichloroacetic acid |
| 11.0 | dimethyl malonate |
| 11.0 | dimethyl oxalate |
| 11.0 | ethyl cyanoacetate |
| 11.0 | neopentyl glycol |
| 11.1 | butanediol-2,3 |
| 11.1 | ethylene oxide |
| 11.1 | nitroethane |
| 11.2 | acetylpiperidine (N) |
| 11.2 | dimethyl-2,2-butanediol-1,2 (Isobutylene glycol) |
| 11.2 | furfural |
| 11.2 | methacrylic acid |
| 11.2 | methylamine |
| 11.3 | dipropyl sulfone |
| 11.3 | methylpyrrolidone-2 (N) |
| 11.4 | acetylpyrrolidine (N) |
| 11.4 | butyl alcohol (normal) |
| 11.4 | cyclohexanol |
| 11.4 | ethylene glycol monomethyl ether |
| 11.4 | tetramethyloxamide |
| 11.5 | formylpiperidine (N) |
| 11.5 | pentanediol-1,5 |
| 11.5 | propyl alcohol (iso) |
| 11.6 | acetylmorpholine (N) |
| 11.6 | butanediol-1,3 |
| 11.8 | allyl alcohol |
| 11.8 | methylene iodide |
| 11.9 | acetonitrile |
| 11.9 | propyl alcohol (normal) |
| 11.9 | Santicizer 8 |
| 12.0 | acrylic acid |
| 12.0 | dimethyl sulfoxide |
| 12.1 | benzyl alcohol |
| 12.1 | butanediol-1,4 |
| 12.1 | butylene-2,3 carbonate |
| 12.1 | diethylene glycol |
| 12.1 | dimethylformamide (N,N) |
| 12.1 | dimethyltetramethylene sulfone |
| 12.1 | formic acid |
| 12.1 | hydrogen cyanide |
| 12.2 | ethylene chlorohydrin |
| 12.3 | ethylacetamide (N) |
| 12.4 | diethyl sulfone |
| 12.4 | methylene glycolate |
| 12.5 | dimethyl phosphite |
| 12.5 | furfuryl alcohol |
| 12.5 | methyl propyl sulfone |
| 12.6 | butyrolactone |
| 12.6 | chloroacetonitrile |
| 12.6 | propylene glycol |
| 12.7 | caprolactam (epsilon) |
| 12.7 | ethyl alcohol |
| 12.7 | nitromethane |
| 12.9 | methyltetramethylene sulfone |
| 13.0 | formylmorpholine (N) |
| 13.1 | dimethylnitroamine (N,N) |
| 13.3 | propiolactone |
| 13.3 | propylene-1,2 carbonate |
| 13.4 | methyl ethyl sulfone |
| 13.4 | pyrone (gamma) |
| 13.4 | tetramethylene sulfone |
| 13.6 | maleic anhydride |
| 13.6 | piperidone |
| 13.7 | diacetylpiperazine (N,N) |
| 13.9 | ethylformamide (N) |
| 14.5 | methanol |
| 14.5 | dimethyl sulfone |
| 14.6 | ethylene glycol |
| 14.6 | methylacetamide (N) |
| 14.7 | ethylene carbonate |
| 14.7 | pyrrolidone (alpha) |
| 15.1 | diformylpiperazine (N,N) |
| 15.4 | succinic anhydride |
| 16.1 | methylformamide (N) |
| 16.3 | ammonia |
| 16.3 | glycerol |
| 19.2 | formamide |
| 23.4 | water |

The above organic solvents with a solubility parameter below about 10, which are miscible with water, can be used at low concentrations in combination with solvents having a solubility parameter above about $10\Delta(cal/cc)^{1/2}$ For the sealing of pharmaceutical gelatin capsules, only pharmaceutically accepted organic solvents are used.

2. Solutions of Salts

Sealing fluids of an aqueous solution of salts or an aqueous organic solution (Organic solvents from TABLE 2 above) of salts, as well as the corresponding acids and/or bases of the salts, are also effective. The water in these sealing fluids may be at a pH range between 1 and 13. The effect of cations and anions of these salts is to depress the melting point of gelatin, as stated by K. H. Gustavson, The Chemistry and Reactivity of Collagen, Academic Press, N.Y. (1956) and may be explained as follows:

(a) Cations like $Ca^{++}$ and $Al^{++}$ are extremely efficient if their share is high and their radius small, which yields a strong polarization according to the Hofmeisters series.

(b) Anions like $SCN^-$ and $I^-$ must possess a large electron cloud in order to have a strong polarizability.

For the sealing of pharmaceutical gelatin capsules, only pharmaceutically acceptable salts are used.

3. Water

Water at a pH range between 1 and 13 is effective as a sealing fluid when thermal energy is applied specifically to the sealing fluid between the body and cap overlap.

4. Polymer Solutions or Emulsions

In addition to the above embodiments the present invention may also include the following polymer solutions or emulsions as claimed in applicant's copending U.S. patent application Ser. No. 444,007, filed Nov. 23, 1982:

a. Polyalkylenes such as polyethylene, polypropylene and the like;
 b. Cellulose, its microcrystalline or form, and derivatives thereof, including cellulose esters such as cellulose acetate, hydroxypropyl-methylcellulose-phthalate, hydroxypropyl-methylcellulose, celluloseacetate-phthalate, cellulose ethers such as lower alkyl cellulose, wherein the lower alkyl group contains from 1 to 3 carbon atoms as for example ethyl cellulose, methylcellulose, other derivatives such as sodium-carboxymethyl-cellulose, and lower hydroxy-alkyl-cellulose wherein the lower alkyl has from 1 to 4 carbon atoms;
 c. Waxes such as carnauba wax;
 d. Polyvinylpyrrolidone;
 e. Polymers and copolymers of acrylic acids and methacrylic acids and salts and esters thereof;
 f. Carbohydrates including mono-, di-, and polysaccharides such as glucose, sucrose, starch, agar, polydextrose, mucopolysaccharides, as well as derivatives of those carbohydrates and the like;
 g. Proteins such as gelatin and hydrolyzed gelatin, with derivatives thereof, soy bean proteins, sunflower proteins, and the like (in addition a protein may be used that has enzymatic activity on the gelatin like protase, preferably collogenase, papain, pepsin, and the like, which causes an enzymatic degradation of the gelatin which results in a seal of the overlap of the cap on body parts);
 h. Shellac;
 i. Rubber;
 j. Polyvinyl-acetates;
 k. Polyuronic acids like alginates and its derivatives;
 l. Polyvinylalcohol;
 m. Cyanoacrylate-monomer; and
 n. Related materials and combinations of the above.

The concentrations of the polymer solutions or emulsions may vary widely and are preferably used as follows:
For dipping: 2–50% by weight
For spraying/jetting: 2–70% by weight
In addition to the polymer solutions or emulsions listed above, the following softeners may also be used:
 a. Poly-hydroxy-alcohols like glycerol, sorbitol, mannitol, and the like;
 b. Dialkylphthalates preferably where alkyl is butyl;
 c. Lower alkyl citrates wherein lower alkyl has 1–6 carbon atoms;
 d. Polyglycols such as polyethyleneglycol and methoxy-propylene-glycol, and 1,2-propyleneglycol;
 e. Esters of polyhydroxy-alcohols such as mono-, di- and tri-acetate of glycerol and the like;
 f. Reocineoleic acid and esters thereof;
 g. Related materials and mixtures of the above.

The above softeners are used in a concentration range of 0.1–20% by weight based on the polymer solutions or emulsions listed above.

In addition to the polymers and the softeners listed above any solvent may also be used that is non-toxic for pharmaceutical capsules and is compatible with the capsule composition. Examples of such solvents include:
a. Organic solvents such as:

(1) Lower alkyl ethers wherein lower alkyl has 1–4 carbon atoms;
 (2) Lower alkyl ketones wherein lower alkyl has 1–8 carbon atoms;
 (3) Methyleneglycol;
 (4) Lower alkyl esters of lower alkyl carboxylic acids wherein the lower alkyl has more than 1–4 carbon atoms; and
 (5) Related materials of the above and lower alkyl alcohols such as ethanol and isopropanol.
b. Water; and
c. Related materials and combinations of the above.

In Groups 1–4 of the above described sealing fluids, surfactants like sodium lauryl sulfate at a concentration within a range of 0.1 to 5% may be added in order to obtain the smallest possible contact angle between the sealing fluid and the capsule material and thus leading to a maximal wettability. Furthermore, the addition of softeners such as glycerol, sorbitol and the like is preferred in some cases in order to get a more flexible seam between body and cap overlap. Furthermore, combinations of the sealing fluids described in groups 1–4 may be used at various mixing ratios.

Methods for the Application of Sealing Fluids to Capsules

Various methods were used for the application of the above sealing fluids for gelatin capsules:

1. Dipping of the entire capsule into a bath of the sealing fluid as shown in FIG. 1 for a time period of 1 to 5 seconds at a temperature range from between about 5° to 70° C. followed by removing of the excess fluid from the capsule surface by a strong air jet. Thereafter, the capsules were dried.

Figure 2:
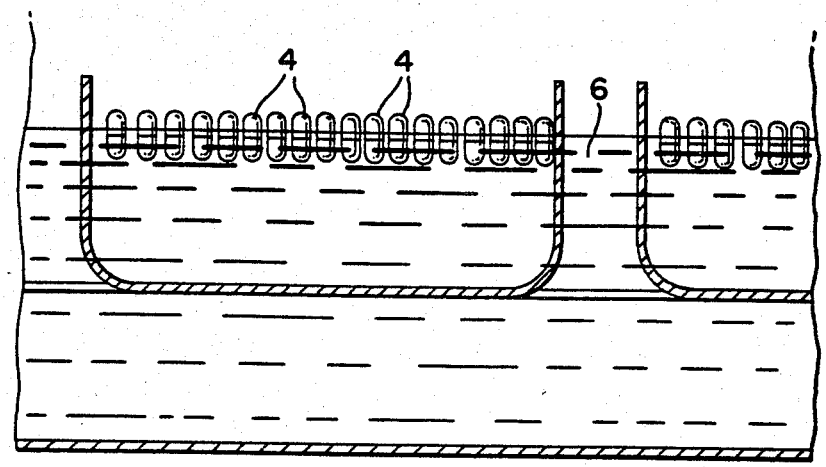
FIG. 2 shows an alternative embodiment of the present invention wherein the filled and telescopically joined capsules 4 are oriented and held with the cap part upright while the overlap of the cap and body part side walls of each capsule 4 are contacted by the sealing fluid 6 within the dipping tank 7.

2. Dipping of the capsules in an upright position as shown in FIG. 2 so that the cap is on top and the overlap of the capsule is in contact with the sealing fluid. The sealing conditions were the same as in paragraph 1 above.

Figure 3:
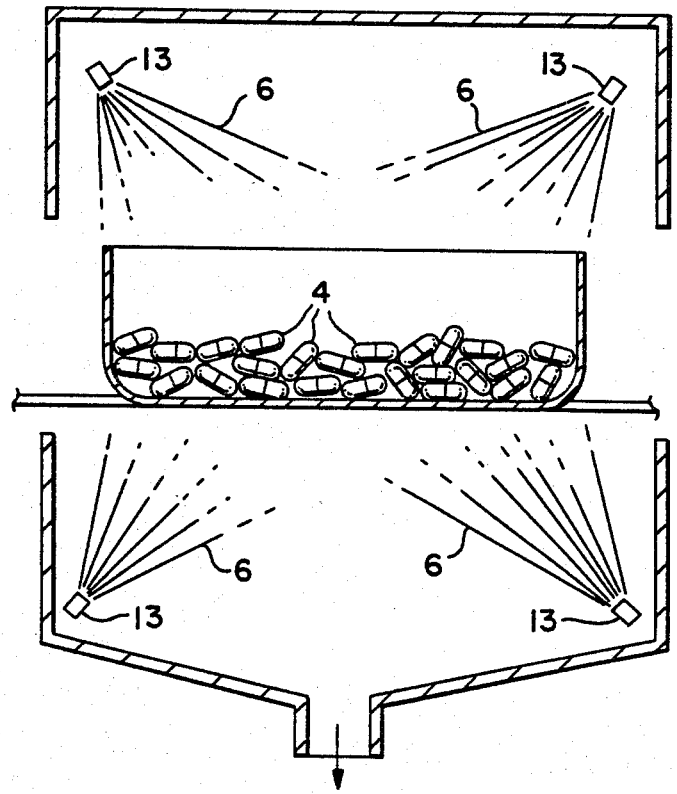
FIG. 3 shows another embodiment of the present invention wherein the filled and telescopically joined capsules 4 are conveyed through a spray chamber 12 wherein sealing fluid 6 is sprayed by nozzle 13 so as to contact the sealing fluid 6 with the overlap of the cap and body 15 part side walls of each capsule 4.

3. Spraying of the capsules with a sealing fluid as shown in FIG. 3. The sealing fluid was used at a temperature range between about 5° to 70° C. After spraying the excess fluid was removed from the capsule surface by a strong air jet (followed by capsule drying, if necessary to remove the sealing fluid from the surfaces of the capsules).

Figure 4:
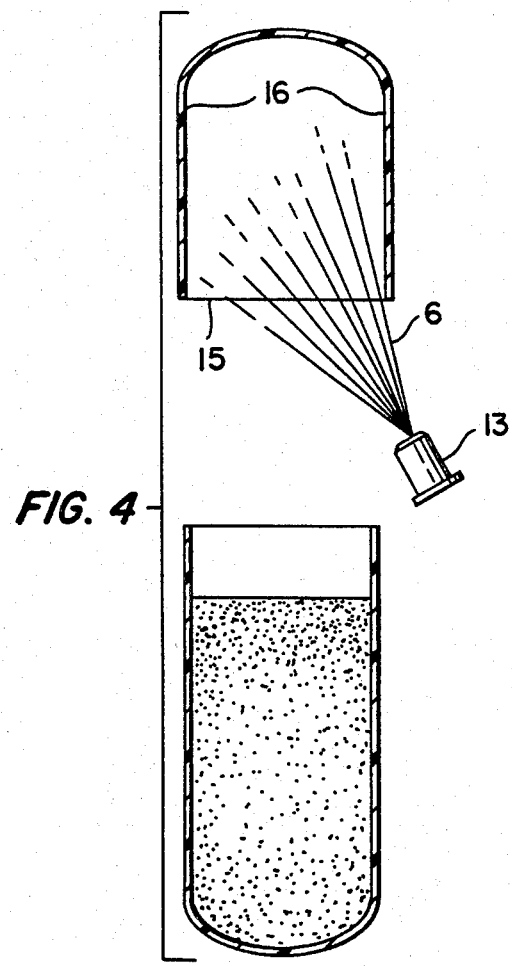
FIG. 4 shows another embodiment of the present invention wherein the sealing fluid 6, or a steam thereof, is sprayed before the capsule 4 is telescopically joined, by a spray nozzle 13 which sprays the sealing fluid 6, or a steam thereof, into the open end 15 and/or onto the inside of the side walls 16 of the cap part 17 of the capsule 4. Alternatively, the sealing fluid or a steam thereof is sprayed into the open end and or onto the outside of the side walls of the body part 19 of the capsule 4. This embodiment of the present invention may be connected to a capsule filling machine.
Figure 5:
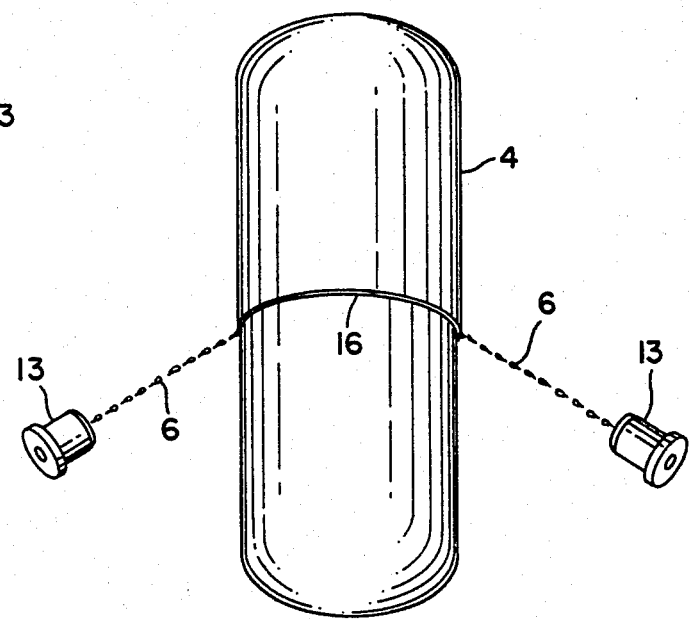
FIG. 5 shows another embodiment of the present invention wherein the sealing fluid 6 is sprayed after the capsule 4 is telescopically joined. The capsule 4 is sealed by spraying the sealing fluid 6 or a steam thereof onto the seam 16 of the overlap of the cap and body part side walls of the capsule 4. This embodiment of the present invention may be connected to a capsule sealing machine or used separately.

4. Application of a sealing fluid to the capsules by using a high frequency pressure pulse jet nozzle as shown in FIGS. 4 and 5 with an accurate monitoring of droplet delivery and deflection. Only minor surface drying was necessary. The sites of application of the sealing fluid were as follows:
into and/or onto the open end of the cap part before capsule joining on a filling machine;
onto the outside of the side walls of the open end of the body part before capsule joining on a filling machine;
onto the overlap of the cap and body parts after capsule joining and filling.

5. Application of a steam of the sealing fluids by a jet nozzle as shown in FIGS. 4 and 5. Only minor surface drying was necessary. The sites of application were the same as in paragraph 4 above.

Capsule sealing by a steam of the sealing fluids selected was also accomplished by exposing the capsules in a combined steam vacuum chamber as disclosed in applicant's copending application, U.S. Ser. No. 440,371, filed Nov. 9, 1982, the disclosure of which is incorporated herein by reference.

The sealing of capsules by the present invention can be used for hard shell gelatin capsules which have been telescopically joined and have the following contents:
a. Empty;
b. Powders;
c. Pastes;
d. Tablets, pellets, granules, microcapsules, etc.
e. Liquids (the sealing of the present invention was also successful in preventing leakage of oil from within the gelatin capsule; and
f. Liquids and solids.

For the sealing of gelatin capsules filled with oils, it was noted that an inverse capillary effect driving the oil between the overlap of the body and cap parts of the gelatin capsules may occur, especially when the filled gelatin capsules are held in a cap part down position. For rape seed oil, having a viscosity of above about 90 centipoises, a contact angle between the gelatin film and the oil was measured which means that the capillary forces of oil are much lower than the capillary forces of the sealing fluids. Therefore, if the gelatin capsules are sealed within a few minutes after filling with an oil, the oily capsule content does not enter between the overlap of the body and the cap of the gelatin capsule. Hence, the capsules can be sealed by the sealing fluids of the present invention.

If liquids or oils with low viscosities below about 90 centipoises and small contact angles are used, the following measures accomplished a complete sealing by the present invention:

sealing the gelatin capsules within a few seconds after ejection from the filling machine.

holding the gelatin capsule in an upright position with the cap part on top during the sealing process, as shown in FIG. 2.

cooling the liquid contents prior to filling into the gelatin capsule in order to increase the viscosity and the contact angle between the gelatin film and the liquid.

adding a thickening agent to the liquid contents prior to the filling process.

The best results were obtained without capsule deformation; with sealing fluids having a high degree of peptization, such as an aqueous solvent of 75% ethanol in water, and also with an aqueous solvent of 90% methanol in water.

The sealing of the overlap of the capsule side walls is accomplished in the present invention as follows:

Gelatin used in the production of capsules contain chains of peptides in the amorphous and the crystalline states. In the crystalline state there is scarcely any translational movement of the center of energy of the chains of peptides. The non-crystallized molecules retain a slight mobility of their chains above the glass transition temperature.

The addition of sealing fluid by capillary action between the side walls of the capsule lowers the melting point of the gelatin or other hydrophilic polymer material. This initiates the movement of the chains of peptides within the overlapping side walls of the capsule and results in a physical bond or seal therein.

By the addition of thermal energy to the chains of peptides in the presence of sealing fluid within the overlapping seam of the capsule the chains of peptides have an increased Brownian movement, resulting in a denaturation of the gelatin or other hydrophilic polymer therein. Upon cooling of the seam the denatured gelatin or other hydrophilic polymer becomes gelatinated or solidified, so as to form a physical bond or seal between the overlapping side walls or seam of the capsule.

In the present invention the preferred manner of adding thermal energy is by electromagnetic irradiation of the chains of peptides in the presence of sealing fluid within the overlapping seal of the capsule. The electromagnetic irradiation found to be most effective was at frequencies of about 2.4 GHz for an exposure of about 1 to 5 seconds with a strength of field in the range of 200 V/cm. It was observed that microwaves of this strength of field and time caused efficient peptization and denaturation of the material within the overlapping seam and resulted in gelatination of the material so as to make a strong physical bond or seal therein.

It was also noted that the use of microwaves at such levels did not deform the capsules. This is explained in that the average water content of capsules is in the range of about 10 to 15%. Such water content is too low to cause a peptization of the gelatin, so as to result in deformation of the entire capsule. At this water content, the melting point of the crystalline chains is not achieved below about 120° C. This temperature is not exceeded by the application of the thermal energy in the present invention.

Alternatively, the addition of thermal energy to the sealing fluid in the overlapping seam can be accomplished by other ranges of frequency of electromagnetic irradiation such as infrared heating; or by convection such as by hot gas or by steam heating; or by conventional conduction heating means such as by electric or by hot water heat directly and locally applied to the overlapping seam of the capsule. A method of conduction heating is to apply a metal stamp or bar, heated in a range of about 120° C. to 180° C. directly to all or part of the overlapping seam for about 1 to 3 seconds. In order to avoid sticking of the metal stamp to the seam, the metal stamp may be coated with a non sticking material such as a tetrafluoroethylene fluorocarbon resin sold under the trademark: TEFLON ®; trademark owned and material supplied by The DuPont Company, Wilmington, Delaware; or a dimethyl silicone sold under the trademark: SILICONE ®; trademark owned and material supplied by the General Electric Company, Schenectady, New York.

In the present invention it was found that an acceptable bond or sealing of the overlap could be obtained without the application of a sealing fluid thereto, provided the thermal energy is locally applied to the overlap, in any of the following ways:

1. Electromagnetic irradiation at frequencies in the infrared range, preferably applied by laser source.

2. Convection, such as by hot gas or by steam heating of approx. 160° C.

3. Conduction, such as by contacting with a metal stamp or bar heated to approx. 180° C.

4. Friction, such as by ultrasonic vibration.

The application of thermal energy to the overlap at the above high levels, without the use of a sealing fluid, must be closely controlled in order to avoid any deformation of the capsule.

EXAMPLE 1

Gelatin capsules, empty and filled with contents as described on page 17 b to e above, and telescopically joined, were sealed by the apparatus shown in FIG. 1 with a sealing fluid of 75% ethanol in water, at room temperature.

No sealing fluid was observed to enter the interior of the telescopically joined capsules during the dipping time of 1 to 5 seconds, and thereafter.

After the elimination of the excess fluid from their surfaces, the capsules were heated with air at a temperature of 70° C. for 60 seconds.

Due to the additional supply of energy through hot air, the inner surface of the cap and the outer surface of the bodies at the overlapping seams of the capsules were completely touching (shrinking of cap part) thus the peptized surfaces formed a high quality capsule seam.

The capsules were tested and found to be all tamper-proof. The capsules with contents as described on page 17 c and e above showed no leakage.

EXAMPLE 2

100 capsules, size 2 (imprinted), were filled with rape seed oil, joined and put on a sieve (diameter 20 cm), the latter being covered by another sieve. The capsules were dipped by a complete immersion of the sieves, during 3 seconds, at room temperature, into a sealing fluid of 60% ethanol and 40% water.

The sealing fluid contained 0.1% of sodium lauryl sulfate as a surfactant decreasing the contact angle between the fluid and the gelatin wall. Immediately after removal from the sealing fluid, the sieve was shaken and together with a strong air jet, the excess fluid was removed from the capsule surface within about 10 seconds. The capsules where then positioned in a hot air drier at 70° C. for 60 seconds.

The capsules were not deformed nor was the imprint faded.

The quality of the capsule seam was tested after 24 hours storage at room temperature and 40% of relative humidity. All capsules tested could not be separated without destroying. Furthermore, no liquid content was leaking from the capsules.

EXAMPLE 3

50 capsules, size 2, were filled with lactose, joined and put on a sieve (diameter 20 cm), the latter being covered by another sieve. The capsules were completely immersed for 3 seconds at room temperature into a sealing fluid of 60% ethanol and 40% water containing 0.1% sodium lauryl sulfate. The excess fluid was removed from the capsule surface within 10 seconds by shaking the sieves and air jetting the capsules, followed by a drying of about 60 seconds under an air flow at 20° C. and 30% relative humidity. Then the capsules were placed on a rolling conveyor which axially aligned the capsules. The capsules were then heated by an infrared lamp for 90 seconds at a temperature of 60° C.

The quality of the capsules and of the capsule seams was similar to the results obtained in example 2.

EXAMPLE 4

100 capsules, size 2, were filled with rape seed oil, joined and placed in a sieve, the latter being covered by another sieve. The capsules were completely immersed for 3 seconds into a sealing fluid consisting of 60% ethanol, 40% water and 0.1% sodium lauryl sulfate at 5° C. The excess fluid was removed from the capsule surface within 10 seconds by a strong air jet at room temperature.

The capsules were then placed on a conveyor system with plastic rolls and moved in an axially vertical position. A wood plate, having a slit of 3 mm, covered the capsules at a distance of about 2 cm whereby the slit was positioned perpendicularly to the axis of, and over, the body and cap overlap. An infrared source was placed over the wood plate in a vertical position over the slit. With this procedure, the body and cap overlap were heated to about 80° C. for 90 seconds resulting in a completely liquid tight and tamper-proof capsule.

The local application of thermal energy at the capsule overlap (without affecting the rest of the capsule) is required for liquid contents which show heat expansion of the contents resulting in an air escape between body and cap during the sealing process.

EXAMPLE 5

50 capsules, size 2, were filled with lactose, joined and placed in a sieve, the latter being covered by a second sieve. The capsules were completely immersed for 3 seconds into a sealing fluid consisting of water and 0.1% sodium lauryl sulfate at 5° C. The excess fluid was removed from the capsule surface by a strong air jet at room temperature and 20% relative humidity for 90 seconds.

In order to form an optimal seal at the overlap, the capsules were irradiated for 3 seconds with electromagnetic energy at 2.4 GHz at a field strength of 171 V/cm. The microwaves of this intensity caused efficient peptization and denaturation of the material within the overlapping seam and resulted in gelatination of the material so as to give a strong physical bond.

EXAMPLE 6

50 capsules, size 2, were filled with rape seed oil, joined and put in a sieve. The capsules were sprayed with a sealing fluid consisting of water containing 0.1% sodium lauryl sulfate at 5° C. After spraying, the sieve was covered by another sieve. The excess fluid from the surfaces were removed by an air jet at room temperature and 20% relative humidity for 90 seconds. For the formation of a strong bond at the body and cap overlap, the capsules were irradiated for 4 seconds with electromagnetic energy (microwaves) at 2.4 GHz at a field strength of 171 V/cm. All capsules proved to be liquid-tight and tamper-proof.

EXAMPLE 7

100 capsules, size 2, were filled with rape seed oil, joined and placed in a sieve with a diameter of 20 cm, the latter being covered by another sieve. The capsules were completely immersed for 3 seconds into a sealing fluid consisting of water containing 0.2 M sodium sulfate and 0.1% of sodium lauryl sulfate at 5° C.

The excess fluid was removed from the capsule surface by a strong air jet at room temperature and 20% relative humidity for 90 seconds.

For the formation of a complete and strong bond at body and cap overlap, the capsules were treated by hot air at a temperature of 70° C. for 60 seconds.

The capsules were both tamper-proof and liquid-tight.

EXAMPLE 8

100 capsules, size 2 were filled with lactose, joined and placed in a sieve with a diameter of 20 cm, the latter being covered with another sieve. The capsules were completely immersed for 4 seconds in a sealing fluid consisting of water containing 0.2 M sodium sulfate ($Na_2SO_4$) and 0.1% sodium lauryl sulfate at 5° C.

The excess fluid was removed from the capsule surface by a strong air jet at room temperature and 20% relative humidity for 90 seconds. In order to form a strong physical bond at the body and cap overlap, the capsules were irradiated for 2 seconds with electromagnetic energy (microwaves) at 2.4 GHz at a field strength of 171 V/cm.

All capsules could not be separated without destroying.

EXAMPLE 9

100 capsules, size 2, were filled with lactose, joined and placed in a sieve with a diameter of 20 cm, the latter being covered by another sieve. The capsules were completely immersed for 3 seconds into a sealing fluid consisting of an aqueous solution of 1.0% hydrolyzed gelatin having an average molecular weight of about 5,000 Dalton (using hydrolyzed gelatin having a molecular weight of 5,000 sold under the trademark: POLYPRO 5000 ®; trademark owned and material supplied by Hormel Inc., Chicago, Illinois) at 5° C.

The excess fluid was removed from the capsule surface by a strong air jet at room temperature and 20% relative humidity for 90 seconds.

For the formation of a strong and lasting physical bond at the body and cap overlap, the capsules were then treated with hot air at a temperature of 70° C. for 60 seconds.

The capsules could not be separated without destroying them.

EXAMPLE 10

100 capsules, size 2, were filled with rape seed oil, joined and placed in a sieve with a diameter of 20 cm, the latter being covered with another sieve. The capsules were completely immersed for 3 seconds in a sealing fluid consisting of an aqueous solution of 1.5% hydrolyzed gelatin having an average molecular weight of about 2000 Dalton (using hydrolyzed gelatin having a molecular weight of 2,000 sold under the trademark: PEPTEIN 2000 ®; trademark owned and material supplied by Hormel Inc., Chicago, Illinois), and containing 0.1% sodium lauryl sulfate at 5° C.

The excess fluid was removed from the capsule surface by a strong air jet, at room temperature and 20% relative humidity for 90 seconds.

For the formation of a strong bond at body and cap overlap, the capsules were irradiated for 4 seconds with electromagnetic energy (microwaves) at 2.4 Hz at a field strength of 171 V/cm.

All capsules proved to be liquid tight and tamper-proof.

EXAMPLE 11

100 capsules, size 2, were filled with rape seed oil, joined and placed in a sieve with a diameter of 20 cm, the latter being covered with another sieve. The capsules were completely immersed for 3 seconds (at 5° C.) into a sealing fluid consisting of an aqueous solution of 1% polyvinyl-pyrolidone (average molecular weight of 25,000 Dalton) containing 0.1% sodium lauryl sulfate.

The excess fluid was removed from the capsule surface by a strong air jet at room temperature and 20% relative humidity for 90 seconds.

For the formation of a strong bond at body and cap overlap, the capsules were irradiated for 4 seconds with electromagnetic energy (microwaves) at 2.4 GHz at a field strength of 171 V/cm.

All capsules proved to be liquid tight and tamper-proof.

EXAMPLE 12

20 capsules, size 2, were filled with lactose and joined.

An acceptable bond of the overlap could be obtained without the application of a sealing fluid thereto by providing the thermal energy locally to the overlap by a metal stamp, coated with TEFLON ®, at a temperature of 180° C. for 1 second.

The stamp treatment was either performed on one or more spots at the circumference of the capsule overlap.

All capsules could not be separated without destroying them. The visible mark left by the stamp made the capsules tamper-evident.

EXAMPLE 13

10 capsules, size 2, were filled with rape seed oil and joined.

A complete bond at a 360° angle of the overlap circumference could be obtained without the application of a sealing fluid thereto by providing the thermal energy locally to the overlap by 3 metal stamps (bars) coated with TEFLON ® each one sealing a segment of 120° at the overlap of the capsule.

With these 3 segmental stamps, a complete ring of a bond at the overlap was obtained thus avoiding the leakage of the liquid content and resulting in a tamperevident capsule.

This invention has been described in terms of specific embodiments set forth in detail, but it should be understood that these are by way of illustration only and that the invention is not necessarily limited thereto. Modifications and variations will be apparent from this disclosure and may be resorted to without departing from the spirit of this invention, as those skilled in the art will readily understand. Accordingly, such variations and modifications of the disclosed invention are considered to be within the purview and scope of this invention and the following claims.

What is claimed is:

1. A method for sealing gelatin capsules having hard shell coaxial cap and body parts which overlap when telescopically joined, comprising the steps of:
    A. dipping the capsules in a sealing fluid making contact by capillary action within the overlap of the cap and body parts;
    B. removing the sealing fluid from the surface of the capsules; and
    C. applying thermal energy locally for about two seconds to the overlap so as to cause peptization or denaturation of the gelatin and sealing fluid within the overlap, thereby causing a sealing together of the cap and body parts.

2. The method for sealing capsules as in claim 1 wherein Step A is spraying the capsules with a sealing fluid.

3. A method for sealing gelatin capsules comprising
    A. exposing the capsules to a sealing fluid in a vacumm-steam chamber;
    B. removing the sealing fluid from the surface of the cap and body parts;
    C. Applying thermal energy locally for about two seconds to the overlap so as to cause peptization or denaturation of the gelatin and sealing fluid within the overlap, thereby causing a sealing together of the cap and body parts.

4. The method for sealing capsules as in claim 1 wherein said sealing fluid is an organic solvent depressing the melting point of gelatin and having a solubility parameter range between about 10 to about 23.4 (calories per cubic centimeter)$^{1/2}$.

5. The method for sealing capsules as in claim 1 wherein said sealing fluid is an aqueous solution of a salt, or the corresponding acids and/or bases of the salt, having cations and anions depressing the melting point of the gelatin.

6. The method for sealing capsules as in claim 4 wherein said sealing fluid is an aqueous solution of said organic solvent and of a salt, or the corresponding acids and/or bases of the salt, having cations and anions of the salt depressing the melting point of the gelatin.

7. The method for sealing capsules as in claim 1 wherein said sealing fluid is water.

8. The method for sealing capules as in claim 1 wherein said sealing fluid is a polymer solution or emulsion.

9. The method for sealing capsule as in any of claims 5–7 wherein the thermal energy is electromagnetic irradiation at frequency of about 2.4 GHz, and with a strength of field of about 200 volts per centimeter.

10. The method for sealing capsule as in any of claims 5–7 wherein the thermal energy is infrared heating.

11. The method for sealing capsule as in any of claims 5–7 wherein the thermal energy is applied by convection heating.

12. The method of sealing a capsule according to claim 4, 5 or 6 wherein the thermal energy is applied by conduction heating of about 170° C.

13. The method for sealing capsule as in claim 12 wherein the thermal energy is the heat content of a metal stamp or bar applied directly to the overlap of the capsule parts.

14. The method for sealing capsule as in claim 13 wherein the hot metal stamp or bar is coated with a nonsticking material such as silicone or TEFLON ®.

15. Apparatus for sealing gelatine capsules, having hard shell coaxial cap and body parts which overlap when telescopically joined, comprising:
a continuous conveyor having container means thereon for receiving the capsules;
wetting means for exposing the capsules to a sealing fluid which enters into the overlap by capillary action;
drying means for removing sealing fluid from the surface of the capsules; and
thermal energy means for heating the sealing fluid and gelatin within the overlap of the cap and body parts so as to cause peptization or denaturation of the sealing fluid and gelatin within the overlap, thereby sealing together the cap and body parts.

* * * * *